US007153490B2

(12) United States Patent
Parente Dueña et al.

(10) Patent No.: US 7,153,490 B2
(45) Date of Patent: Dec. 26, 2006

(54) LIPOSOMES ENCAPSULATING ANTICANCER DRUGS AND USE THEREOF IN THE TREATMENT OF MALIGNANT TUMORS

(75) Inventors: Antonio Parente Dueña, San Just Desvern (ES); Ferran Pons Lambiez, Molins de Rei (ES); Angels Fabra Fres, Barcelona (ES); María Dolores Polo Trasancos, Barcelona (ES); Josep Garces Garces, Martorell (ES); Francesca Reig Isart, Barcelona (ES)

(73) Assignee: Lipotec, SA (ES)

( * ) Notice: Subject to any disclaimer, the term of this patent is extended or adjusted under 35 U.S.C. 154(b) by 502 days.

(21) Appl. No.: 10/398,627

(22) PCT Filed: Oct. 3, 2001

(86) PCT No.: PCT/ES01/00367

§ 371 (c)(1),
(2), (4) Date: Jul. 11, 2003

(87) PCT Pub. No.: WO02/30397

PCT Pub. Date: Apr. 18, 2002

(65) Prior Publication Data

US 2005/0100590 A1 May 12, 2005

(30) Foreign Application Priority Data

Oct. 10, 2000 (ES) .................................. 20002447

(51) Int. Cl.
*A61K 9/127* (2006.01)
(52) U.S. Cl. ....................... 424/1.69; 424/450; 514/12; 514/13; 530/326
(58) Field of Classification Search .................... 514/2
See application file for complete search history.

(56) References Cited

U.S. PATENT DOCUMENTS 5,605,703 A 2/1997 Lambiez et al. ............ 424/450

FOREIGN PATENT DOCUMENTS

| EP | 0274174 | 7/1988 |
|---|---|---|
| WO | 85/00968 | 3/1985 |
| WO | 86/04232 | 7/1986 |
| WO | 92/02208 | 2/1992 |
| WO | 98/16198 | 4/1998 |

OTHER PUBLICATIONS

Manning et al. Review: Stability of protein pharmaceuticals. Pharm. Res., 6(11), 903-17, 1989.*
D.S. Grandt, et al., "Interaction of Endothelial Cells With A Laminin A Chain Peptide (SIKVAV) in Vitro and Induction of Angiogenic Behavior in Vivo", *Journal of Cellular Physiology*, vol. 153, No. 3, 1991, pp. 614-625.
International Search Report PCT/ES01/00367.
T.M. Allen et al., "Liposomes with prolonged circulation times: factors affecting uptake by reticuloendothelial and other tissues," Biochimica et Biophysica Acta. 981:27-35 (1989).
T.M. Allen et al., "Uptake of liposomes by cultured mouse bone marrow macrophages: influence of liposome composition and size," Biochimica et Biophysica Acta. 1061:56-64 (1991).
S. Dedhar et al., "Alterations in Integrin Receptor Expression on Chemically Transformed Human Cells: Specific Enhancement of Laminin and Collagen Receptor Complexes," The Journal of Cell Biology 110:481-189 (1990).
E.A. Forssen et al., Proc. Natl. Acad. Sci. USA 78:1873-1877 (1981).
E.A. Forssen et al., "Improved Therapeutic Benefits of Doxorubicin by Entrapment in Anionic Liposomes," Cancer Research 43:546-550 (1983).
E.A. Forssen et al., "Attenuation of Dermal Toxicity of Doxorubicin by Liposome Encapsulation," Cancer Treatment Reports 67:481-484 (1983).
A. Gabizon et al., "Liposomes as *in vivo* Carriers of Adriamycin: Reduced Cardiac Uptake and Preserved Antitumor Activity in Mice," Cancer Research 42:4734-4739 (1982).
A. Gabizon et al., "Enhancement of Adriamycin Delivery to Liver Metastatic Cells with Increased Tumoricidal Effect Using Liposomes as Drug Carriers," Cancer Research 43:4730-4735 (1983).
A. Gabizon et al., "Superior Therapeutic Activity of Liposome-Associated Adriamycin in a Murine Metastatic Tumour Model," Br. J. Cancer 51:681-689 (1985).
A. Gabizon et al., "Comparative Long-Term Study of the Toxicities of Free and Liposome-Associates Doxorubicin in Mice After Intravenous Administration," J. Natl. Cancer Inst. 77(2):459-467 (1986).
E. Mayhew et al., "Effect of Liposome Entrapped Chemotherapeutic Agents on Mouse Primary and Metastatic Tumors," Biol. Cell 47:81-85 (1983).
F. Olson et al., "Characterization, Toxicity and Therapeutic Efficacy of Adriamycin Encapsulated in Liposomes," Eur. J. Cancer Clin. Oncol. 18(2):167-176 (1982).
A. Rahman et al., "Liposomal Protection of Adriamycin-Induced Carciotoxicity in Mice," Cancer Research 40:1532-1537 (1980).
A. Rahman et al., "Pharmacological, Toxicological, and Therapeutic Evaluation in Mice of Doxorubicin Entrapped in Cardiolipin Liposomes," Cancer Research 45:796-803 (1985).
C. Storm et al., "Influence of Lipid Composition on the Antitumor Activity Exerted by Doxorubicin-Containing Liposomes in a Rat Solid Tumor Model," Cancer Research 47:3366-3372 (1987).

(Continued)

*Primary Examiner*—Cecilia J. Tsang
*Assistant Examiner*—Maury Audet
(74) *Attorney, Agent, or Firm*—Ostrolenk, Faber, Gerb & Soffen, LLP

(57) ABSTRACT

Liposomes encapsulating anticancerous drugs and the use thereof in the treatment of malignant tumors. The liposomes are coated with a lipopeptide composed of three substructures: a lipid fragment, an active oligopeptide and an oligopeptide spacer between the other two fragments. Applicable in intravenous administration for treatment of malignant tumors.

24 Claims, 3 Drawing Sheets

OTHER PUBLICATIONS

Figure 1:
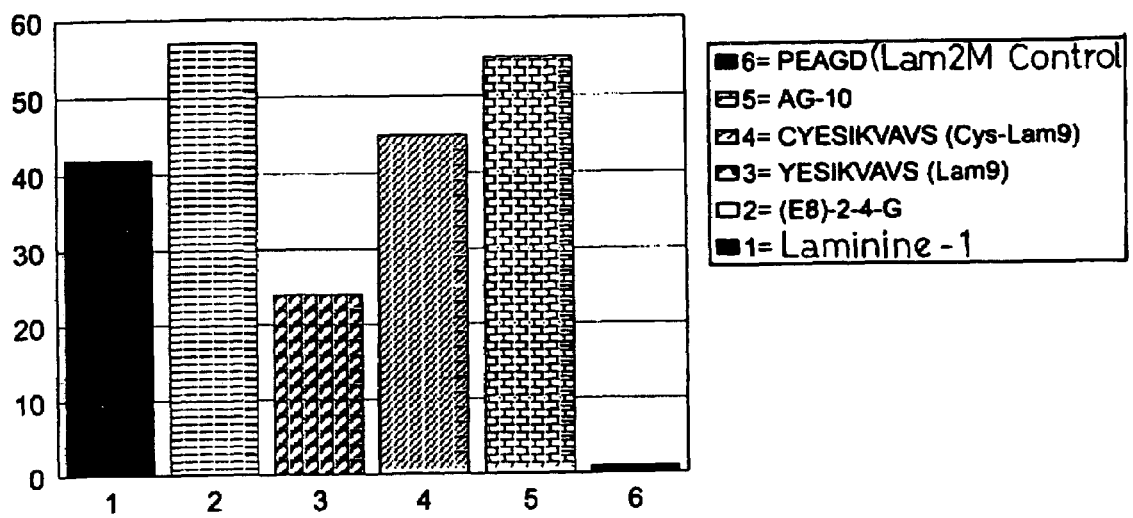

Q.G.C.M. van Hoesel et al., "Reduced Cardiotoxicity and Nephrotoxicity with Preservation of Antitumor Activity of Doxorubicin Entrapped in Stable Liposomes," Cancer Research 44:3698-3705 (1984).

R.C. Young et al., "The Anthracycline Antineoplastic Drugs," N. Eng. J. Med. 305(3):139-153 (1981).

T.M. Allen et al., "Liposomes containing synthetic lipid derivatives of poly(ethylene glycol) show prolonged circulation half-lives in vivo," Biochimica et Biophysica Acta 1066:29-36 (1991).

G. Blume et al., "Liposomes for the sustained drug release in vivo," Biochimica et Biophysica Acta 1029:91-97 (1990).

E.G. Mayhew et al., "Effects of Liposome-Entrapped Doxorubicin on Liver Metastases of Mouse Colon Carcinomas 26 and 38," JNCI 78(4):707-713 (1987).

A. Mori et al., "Influence of the steric barrier activity of amphipathic poly(ethyleneglycol) and ganglioside $GM_1$ on the circulation time of liposomes and on the target binding of immunoliposomes in vivo," FEBS 284(2):263-266 (1991).

A. Rahman et al., "Antitumor and toxicity evaluation of free doxorubicin and dosorubicin entrapped in cardiolipin liposomes," Cancer Chemother. Pharmacol. 16:22-27 (1986).

* cited by examiner

SEQUENCE LISTING

```
<160> NUMBER OF SEQ ID NOS: 5

<210> SEQ ID NO 1
<211> LENGTH: 8
<212> TYPE: PRT
<213> ORGANISM: Artificial
<220> FEATURE:
<223> OTHER INFORMATION: Synthetic construct

<400> SEQUENCE: 1

Ala Ala Ala Ala Ala Cys Tyr Glu
1               5

<210> SEQ ID NO 2
<211> LENGTH: 8
<212> TYPE: PRT
<213> ORGANISM: Artificial
<220> FEATURE:
<223> OTHER INFORMATION: Synthetic construct

<400> SEQUENCE: 2

Ser Ser Ala Ala Ala Cys Tyr Glu
1               5

<210> SEQ ID NO 3
<211> LENGTH: 9
<212> TYPE: PRT
<213> ORGANISM: Artificial
<220> FEATURE:
<223> OTHER INFORMATION: Synthetic construct

<400> SEQUENCE: 3

Arg Lys Glu Arg Lys Glu Cys Tyr Glu
1               5

<210> SEQ ID NO 4
<211> LENGTH: 7
<212> TYPE: PRT
<213> ORGANISM: Homo sapiens

<400> SEQUENCE: 4

Ser Ile Lys Val Ala Val Ser
1               5

<210> SEQ ID NO 5
<211> LENGTH: 15
<212> TYPE: PRT
<213> ORGANISM: Artificial
<220> FEATURE:
<223> OTHER INFORMATION: Synthetic construct

<400> SEQUENCE: 5

Ala Ala Ala Ala Ala Cys Tyr Glu Ser Ile Lys Val Ala Val Ser
1               5                   10                  15
```

LIPOSOMES ENCAPSULATING ANTICANCER DRUGS AND USE THEREOF IN THE TREATMENT OF MALIGNANT TUMORS

FIELD OF THE INVENTION

The present invention is related with procuring a system of anti-cancerous treatment capable of destroying selectively the cancerous cells inside a living being without affecting the remaining cells of the treated organism. More particularly, the invention is related with liposomes containing anti-cancerous drugs of utility in the aforementioned treatment.

STATE OF THE TECHNIQUE

Cancer is one of the most widespread illnesses in developed countries and, specifically, tumoral metastases are the main cause of mortality in patients with solid malignant tumours. They consist of the appearance of a new cancerous centre, starting from a primary tumour, in another organ or different tissue. This metastasic process includes a series of sequential stages in which the tumoral cells must interact with the cellular components and the tissues of the host. These stages are as follows: separation of tumoral cells from a primary tumour; invasion of intravascular space; migration through the vascular or lymphatic system to other tissues; adhesion to the vascular endothelium; extravasation and invasion of the new tissue; and formation of the secondary tumour.

Throughout this process, the metastasic tumoral cells interact with the components of the extracellular matrices and, specifically, with the basal membranes, through their adhesion thereto, provoking their deterioration through the action of proteolytic enzymes produced by themselves and/ or by the actual host cells, stimulated by the tumoral cells. Thus, the alteration to the cellular adhesion properties is an indispensable element for the appearance of metastasis, since it is a process tied to the liberation of cells from the initial tumour, to their migration and to their implantation in new tissue.

The principal molecules of adhesion that intervene in this interaction are the integrins. The integrins are a family of transmembrane glycoproteins, formed by two chains $\alpha$ and $\beta$ joined by non-covalent bonds (hydrophobes). Among other functions, the integrins act a receptors of determined proteins of the extracellular matrix, like the Lamanin, the Fibronectin, the Vitronectin and the Collagen (Ruoslahti, E., Giancotti, F. G., Cancer Cells (1989), 1, 4, 119–126). Recently that a change in the expression of the integrins in the tumoral cells has been demonstrated whereby their presence in this type of cell is increased (Dedhar, S., Saulmier, R., Cell Biol. (1990), 11, 481–489). This increase is the responsible factor for the adhesion to the extracellular matrix and for the acquisition of metastasic potential.

The main treatment employed for the elimination of tumours is the administration of cytostatics by endovenous route, particularly those belonging to the anthracycline family (Young, R. C., Ozols, R. F., Myers, C. E., N. Eng. J. Med. (1981), 305, 139–153). But, due to their lack of selectivity with respect to the tumoral cells, to the development of resistance to these drugs by the malignant cells and to the different response of the primary tumour and of the metastasis with respect to their action, this type of therapy usually gives rise to the appearance of serious secondary effects, some of which are of a chronic or irreversible nature.

Consequently, the main objective of current chemotherapy centres on achieving an enhanced antitumoral effectiveness and reducing the toxicity of these drugs. One way of doing this could consist in getting the cytostatic, in a suitable concentration, to reach the target cells, resulting in the selective destruction of the primary tumour or the metastases without any healthy cell being affected. In this manner an increased therapeutic index of the drug would be produced and more effective therapies achieved.

In these systems the drug is incorporated in the liposome aqueous spaces when it is hydrophilic or it is distributed between these and the lipid bilayers when it has a more lipophilic character. Once the drug is encapsulated, it can be administered to the patient under treatment.

Various researchers have shown that the use of liposomes for the administration of antineoplastics often enhances the traditional methods of administration, see, for example: Gabizon et al.: Cancer Res. (1982) 42, 4734–4739 and Van Hossel et al.: Cancer Res. (1984) 44, 3698–3705.

It has been observed, by means of the employment of various animal models, that the encapsulation of doxorubicin in liposomes reduces significantly the secondary effects of toxicity, both chronic and acute. See, by way of example, Rahman et al.: Cancer Res. (1980) 40, 1532–1537, Forssen et al.: Proc. Natl. Acad. Sci. USE (1981) 78, 1873–1877, Olson et al.: Eur. J. Cancer Clin. Oncol. (1982) 18 167–176, Rahman et al.: Cancer Res. (1985) 45, 796–803 and Gabizon et al.: J. Natl. Cancer Inst. (1986) 77, 459–467. Additionally, other toxicity indicators, such as alopecia, weight loss, nausea, vomiting, and also dermal necrosis by extravasation can be reduced in a significant manner with the administration of doxorubicin in liposomes. Forssen et al.: Cancer Treat. Rep. (1983) 67, 481–484; see also the references cited above in this paragraph.

It has likewise been established in various tumoral models that this significant reduction in toxicity is not produced at the expense of a diminution in antitumoral effectiveness. As well as the references cited above, see Rahman et al.: Chemother. Pharmacol. (1986) 16, 22–27, Gabizon et al.: Cancer Res. (1983) 43, 4730–4735 and Br. J. cancer (1985) 51, 681–689, Mayhew et al.: J. Natl. Cancer Inst. (1987) 78, 707–713, Forssen et al.: Cancer Res. (1983) 43, 546–550, and Storm et al.: Cancer Res. (1987) 47, 3366–3372.

Given the incidence and the special characteristics of the cancerous metastases, antimetastasic therapy is one of the fields in which most effort has been applied in the hunt for new alternatives to conventional treatments. For their mechanisms of action, their proven high effectiveness and their high toxicity, the anthracyclines form the family of cytostatics most studied in the field of drug encapsulation in controlled release systems such as the liposomes, which can be appreciated from the growing number of patents that have been appearing under this heading, of which 80% of the total of those existing for liposomes are applied to cytostatics.

The first generation of liposomes containing anthracyclines corresponded to vesicles formed by PC, PG and cholesterol, in the aqueous interior space of which the drug was encapsulated. These liposomes showed a diminution in the toxicity of the drug, though their antitumoral activity was no greater than that of the free drug, they only improved the activity of the drug in the case of tumoral models in which the metastasic cells were spread through the liver, the most accessible organ for the liposomes, but not when the tumoral growth is local (Mayhew, E., Rustum, Y., Biol. Cell. (1983), 47, 81–86). In addition, due to their rapid capture by the macrophages of the endoplasmatic reticle, their permanence in the organism after the intravenous injection was reduced to a few hours. For this reason, and despite the intensive research carried out, that has been no formulation to satisfy the expectations initially placed on liposomes as transporters of cytostatics. It was during the eighties that the situation changed with the appearance of the first publications in which liposomes were described that presented glycolipids (Allen, T. M., Hansen, C., Rutledge, J., *Biochem. Biophys. Acta* (1989), 981, 27–35; Mori, A., Klivanov, A. L., Torchilin, V. P., Huang, L., *FEBS Lett.* (1991), 284, 263–266) or hydrophilic polymers like the polyethylene glycol (PEG) (Blume, G., Ceve, C., *Biochem. Biophys. Acta* (1990), 1029, 91–97, Allen, T. M., Hansen, C., Martin, F., Redemann, C., Yau-Young, A., Biochem. Biophys. Acta (1991), 1066, 29–36) on their surface for the purpose of augmenting their time of circulation in the blood stream, obtaining thereby the so-called "second generation liposomes" or "stealth liposomes". It seems this stabilising effect of the PEG and the glycolipids is due to their hydrophilic properties which prevent aggregates being formed on the surface of the liposome and permit it not to be recognised as ligand of any cellular receptor nor of any plasmatic protein. Moreover, their presence on the surface of the liposomes produces a steric effect, as it hinders the action of the opsonins and other blood proteins, and reduces the accessibility of the macrophage receptors to the phosphate groups of the phospholipids, which results in an increased time of circulation in the blood.

Subsequently some authors found that it was possible to improve the stability and effectiveness characteristics of these liposomes through the incorporation of additives which inhibited lipid peroxidation like vitamin E acetate, BHT or those derived from chromans (EP-0274174, WO-8500968, WO-9202208 and U.S. Pat. No. 5,605,703).

Despite the fact that these galenic forms offered a series of benefits over conventional forms, there remains pending the possibility of steering the vesicles to target cells in order to improve the effectiveness with smaller drug doses and of suppressing or reducing secondary effects.

The basic idea is to incorporate on the surface of the liposome any chemical body capable of being recognised selectively by the target cells. The success in steering the liposomes toward the target cells resides in an adequate choice of vector molecule.

The process of selecting any chemical structure capable of steering the liposomes to tumoral cells is by no manner trivial, as specifically in the case of tumoral cells there exists a great diversity of proteins located in the membrane as well as of antigens and surface receptors that vary according to the metastasic potential, the proliferating activity and the tissue in question, in such a manner that, although they could be used as a base for selecting recognition structures, in practice the choice is not immediate. Furthermore, in many cases, the true situation is that the proliferating and/or tumoral cells have as a differentiating feature the over-expression of determined structures with respect to normal cells.

Knowledge accumulated to date indicates that the adhesion processes and the proteins involved play an essential role in the development of the metastasic process and of the necessary vascularization for cellular proliferation.

From among the proteins most involved in these mechanisms, Laminin has proved to be a good candidate for steering liposomes, since it has been conclusively shown that its receptors are over-expressed in the tumoral cells.

Laminin is the majority component of the basal membrane of cells after collagen. It is a glycoprotein formed by three polypeptide chains: α (440 kDa), β (200 kDa) and γ (220 kDa), which are arranged in the shape of a cross, with two short arms and one long arm. The bonds between the chains are formed by di-sulphide links and by interactions of the non-covalent type, forming an asymmetric molecule in which different structural domains are located.

The cells have different specific membrane receptors that recognise peptide sequences and/or functional domains of the molecule of the Laminin. These receptors can be classified into two groups: integrins and non-integrins.

The integrins are formed by two trans-membrane polypeptide chains, α and β, in non-covalent association. These molecules are the receptors through which the cells adhere to the components of the extracellular matrix. Some of them also intervene in the cell-to-cell recognition. Each one recognises specific peptide sequences which are present in the molecules of the matrix, like for example Laminin.

Among the non-integrin-type receptors, that most studied is the receptor for 67 kDa for Laminin, and it has been isolated and identified starting from various cellular tissues, among which are the carcinomas. Moreover, it has been verified that the metastasic tumoral cells express on their cellular surface more receptors for Laminin than normal cells, for which reason this receptor could be considered to be a marker of tumoral progression and an indicator of the aggressivity of many types of tumour.

The Laminin presents various metastasic activities, such as:
  causing cellular adhesion, growth and extension;
  stimulating the distinction between epithelial and tumoral cells;
  provoking cellular migration;
  facilitating malignancy of tumoral cells by their presence on the surface, which makes their invasivity and metastasic activity increase.

Determined studies have shown the different functions of Laminin are mediatized by specific peptide sequences present in the Laminin molecule, such as: the sequence of seven amino acids SIKVAVS SEQ ID NO: 4, that is found located in the fragment PA22-2 of the Laminin α chain. Specifically the most active zone of this region is the heptapeptide SIKVAVS SEQ ID NO: 4.

SUMMARY OF THE INVENTION

At present, studies on liposomes are directed at their steering towards or targeting of tumoral cells through incorporation on the surface of the ligand vesicles, as may be antibodies, peptides and proteins, capable of recognising and linking specifically with this type of cell (Allen T. M., Austin, G. A., Chonn, A., Lin, L., Lee, K. C., *Biochem. Biophys. Acta* (1991), 1061, 56–63).

Thus, the object of the present invention consists of a new application for anticancerous drugs encapsulated in liposomes, which present as main characteristic their being covered by lipopeptides proceeding from the structure of the laminins—especially the SIKVAVS SEQ ID NO: 4 sequence—in such a manner that the liposomes so prepared demonstrate a high selectivity regarding tumoral cells and therefore increase the effectiveness of the encapsulated anticancerous drug.

| MEANING OF THE ABBREVIATIONS USED IN THE INVENTION | |
|---|---|
| DXR: | Doxorubicin |
| PC: | Phosphatidylcholine |

-continued

MEANING OF THE ABBREVIATIONS USED IN THE INVENTION

| PL: | Phospholipids of hydrogenated egg | |
|---|---|---|
| PG: | Phosphatidylglycerol | |
| CHOL: | Cholesterol | |
| CROM: | Chroman-6 | |
| A | Ala | Alanine |
| C | Cys | Cisteine |
| D | Asp | Aspartic acid |
| E | Glu | Glutamic acid |
| F | Phe | Phenylalanine |
| G | Gly | Glycin |
| H | His | Histidine |
| I | Ile | Isoleucine |
| K | Lys | Lysine |
| L | Leu | Leucine |
| Lam2M: | myristoyl-PEGAD (SEQ ID NO: 6) | |
| Lam9: | myristoyl-YESIKVAVS (SEQ ID NO: 7) | |
| Lam9Cys: | myristoyl-CYESIKVAVS (SEQ ID NO: 8) | |
| Lam9Cys-b-Ala: | myristoyl-AAAAACYESIKVAVS (SEQ ID NO: 5) | |
| AG10: | GYSRARKEAASIKVAVSARKE (SEQ ID NO: 9) | |
| (E8)-2-4G: | NPWHSIYITRFG (SEQ ID NO: 10) | |
| mir: | myristoyl | |
| DOX: | Doxorubicin | |

DETAILED DESCRIPTION OF THE INVENTION

The present invention is related with the preparation and use of liposomes containing anticancerous drugs.

The liposomes of the present invention have as their main characteristic that they are coated with fragments of hydrophobically derivatized peptides (overlaid lipopeptides) in such a manner that the liposome so prepared offer a high targeting capability with regard to tumoral cells, thereby increasing the effectiveness of the encapsulated anticancerous drug.

Surprisingly it was shown that the active overlaid lipopeptides in vitro prior to being incorporated in liposomes, would totally lose their targeting capability when incorporated in liposomes, for which reason, according to the invention, peptide spacers were developed which, intercalated between the sequence and the lipophile chain of the overlaid lipopeptide would, strangely, permit the targeting ability of the active peptide sequence to be maintained.

In this way the structure of the overlaid lipopeptide (hydrophobically derivatized peptide) is as follows:

| Lipid Fragment | Spacer | Active Sequence |
|---|---|---|

Consequently, the object of the present invention resides in the preparation and use of liposomes containing anticancerous drugs which on their surface have peptide fragments derivatized from Laminin (overlaid lipopeptides), made up of the following three structural blocks: a lipid fragment, an active oligopeptide and an oligopeptide spacer among other fragments.

The lipid fragments are fatty acids of carbonated chain length between C6 and C20. More specifically decanoyl, myristoyl and stearoyl.

The spacer fragment consists of oligopeptides inactive with respect to Laminin having a length lying between five and ten amino acid residues. More specifically, with a length of seven to nine amino acid residues, and more specifically the sequences AAAAACYE, SSAAACYE and RKERKECYE.

The active sequence consists of the oligopeptide SIKVAVS.

The liposome-forming lipids are well known. Generally phospholipids are included, with net neutral or negative charge, and a sterol, like cholesterol. The choice of the lipids is performed based on the requirements with respect to the final liposome size, to the drug to be encapsulated and to the desired stability for the preparation. Usually the largest lipid component of the liposomes is the phosphatidyl choline (PC). The PCs differ from each other in the length and degree of saturation of their acylic chains and can isolated from natural or synthesised sources. The inclusion of a negatively charged phospholipid favours the stability of the liposome solution and prevents the spontaneous aggregation of the liposomes.

The negatively charged phospholipids most employed are the phosphatidyl glycerol (PG), phosphatidyl serine (PS) and the phosphatidyl inositol (PI), among others. The proportion used, of neutral phospholipid to negatively charged phospholipid ranges from 10:2 to 10:10 respectively. The inclusion of cholesterol generally favours the stability of the liposomes by causing the permeability of the membrane to diminish with respect to ions and small polar molecules and likewise reduces the penetration capacity of a series of proteins between the bilayers that could result in a greater disorder among these. Typically the proportion of cholesterol used runs from 0 to 50% of total lipids.

Optionally, the liposomes object of the present invention, can contain additives that permit enhancement of their stability properties or reduce the toxicity of the encapsulated drug. For example, mention can be made of the lipid oxidation inhibitors such as those described in the patents U.S. Pat. No. 5,605,703, EP 0274174, WO-8500968 and WO 9202208.

The anticancerous drugs that can be encapsulated in the liposomes of the present invention include, but are not limited to:

Nirogenated mustard analogues like Cyclophosphamide; Melphalan; Iphosphamide; or Trophosphamide;

Ethylenimines like Thiotepa;

Nitrosoureas like Carmustine;

Leased agents like Temozolomide; or Dacarbazine;

Analogous antimetabolites of Folic acid like Methotrexate or Raltitrexed;

Analogues of Purines like Thioguanine, Cladribine or Fludarabine;

Analogues of Pyrimidines like Fluorouracil, Tegafur or Gemcitabine;

Alkaloids of Vinca and analogues like Vinblastine, Vincristine or Vinorelbine;

Derivatives of Podophyllotoxin like Etoposide, Taxanes, Docetaxel or Paclitaxel;

Anthracyclines and similar like Doxorubicin, Epirubicin, Idarubicin and Mitoxantrone;

Other cytotoxic antibiotics like Bleomycin and Mitomycin;

Platinum compounds like Cisplatin, Carboplatin and Oxaliplatin;

Monoclonal antibodies like Rituximab;

Other antineoplastic agents like Pentostatin, Miltefosine, Estramustine, Topotecan, Irinotecan and Bicalutamide.

In accordance with that described above, the liposomes of the present invention present the following characteristics:

a) A lipid concentration of 1 and 100 mg/ml, and preferably around 10 mg/ml.

b) The component lipids are phospholipids, of both natural and synthetic origin, and cholesterol.

c) The proportion of cholesterol, with respect to the quantity of total lipids, is between 0 and 50%, preferably between 35 and 50%.
d) The phospholipids present are phosphatidyl choline, which has no net charge, and optionally another, negatively-charged phospholipid, preferentially phosphatidyl glycerol.
e) The ratio of the neutral phospholipid to that negatively charged lies between 10:2 and 10:10 and preferably between 10:7 and 10:10 respectively.
f) Optionally the liposomes can contain other additives like for example lipid oxidation inhibitors like those described in the patents U.S. Pat. No. 5,605,703, EP 0274174, WO-8500968 and WO-9202208.
g) The concentration of peptide would oscillate between 0.1 and 1 mg/ml, and preferably around 0.5 mg/ml.
h) The liposomes are formed in an aqueous solution, tamponed or not, physiologically isotonic. For example, 0.9% NaCl.
i) The size of the liposomes shall be in any case less than 500 nm, and preferably less than 300 nm and more specifically between 50 nm and 250 nm.

Preparation of the Liposomes and Incorporation of the Drug:

A preferred method is that presented by Bangham et al. in which multilamellar liposomes (MLVs) are obtained which heterogeneous in size. In this method the forming lipids are dissolved in a suitable organic solvent that is subsequently removed by rotary evaporation under vacuum. The lipid film formed is subjected to hydration with an adequate aqueous medium containing the drug, by means of manual or mechanical agitation. The heterogeneous suspension of MLVs is subjected to whatever of the known procedures for reduction and homogenisation of sizes. For example, two preferred procedures are that of sonication with Titanium probe to obtain SUV liposomes and the extrusion through polycarbonate filters of the MLV solution to obtain VET liposomes.

Preparation of the Peptide Fragments:

The sysnthesis of the peptides is carried out using the solid phase method of Merrifield (1962) with Fmoc/tBu approach.

Incorporation of Lipopeptide:

The lipopeptides employed were acyl-oligopeptides, being of preference the acyl group with linear saturated hydrocarbon chains of length C6 to C20—preferentially the decanoyl, myristoyl or stearoyl. The lipopeptides were mixed with the rest of the components that were to constitute the liposomes, or else they were incorporated in the liposomes by incubation at 60° C. of these lipopeptides and the vesicles, since, as the bilayers were in a gel state, permitted the incorporation of the hydrophobic part of these derivatives in their interior. In both cases the hydrophobic zone of the derivatives ought to remain forming the bilayer, whilst the peptide sequence would remain on the hydrophilic exterior.

By way of illustration, but not restrictively, the procedure detailed in the present patent is described hereunder by means of several practical examples.

EXAMPLE 1

Synthesis of Active Peptides with Carboxylic End

The synthesis of peptides derived from Laminin is carried out following the solid phase method of Merrifield (1962) with Fmoc/tBu approach.

In order to obtain a sequence with carboxylic end, as the solid synthesis support, a Wang resin is employed with a degree of functionalisation of 0.72 meq/g of resin which was submitted to the treatment outlined in the table below:

TABLE 1

Washing protocol for the peptidyl resin

| Step | Reagent | Repetitions | Time |
|---|---|---|---|
| 1 | DMF | 3 times | 1 minute |
| 2 | Dichloromethane | 3 times | 1 minute |
| 3 | Tertiary amyl alcohol | 3 times | 1 minute |
| 4 | Ether | Until dry | — |

In general, the starting point was 1 gram of Wang resin in a syringe with a filter coupled to a vacuum system, and it was dimethylformamide (DMF) was blown in for 30 minutes. In parallel, in a filter weight scale, the necessary amount was weighed of the first Fmoc-amino acid and it was dissolved in DMF, adding to this solution the coupling agents 4-dimethyl amino pyridine (4-DMAP) and diisopropylcarbodiimide (DIPCDI) (0.3:1, molar). All the reagents were used in an excess of 5 times with respect to the quantity required to complete the reaction. Thereafter, this mixture was added to the previously drained resin and left to react for 2 hours at room temperature with occasional stirring. After this time the resin was washed with different solvents until completely dry.

Finally the joint quantity of amino acid was evaluated. In the cases where the reaction was incomplete, more reagents were added, in a quantity corresponding to one half the initial quantity employed, and left to react for a further two hours, repeating thereafter the same process of resin-drying and quantifying of the amino acid incorporated.

The union of the remaining Fmoc-amino acids was carried out through successive stages of deprotection of the amino group and formation of the amide bond.

Thus, for the suppression of the Fmoc amino protector group, the peptidyl-resin was treated once with DMF/piperidine 20% for a minute, the treatment being repeated a second time for 5 minutes. Afterwards, the piperidine was removed with various washings with DMF and the ninhydrin test was carried out to check for the complete elimination of the Fmoc group (blue colouring). In some cases the deprotection was performed with the reagent 1.8-diazabicyclo [5.4.0.]-undec7-eno (DBU) used in the mixture of DMF/piperidine/DBU (48:2:2, v/v/v) by means of a single treatment of the resin for 7 minutes. At the end of this time the resin was washed various times with DMF and the ninhydrin test performed again just as in the previous case.

Once the peptidyl-resin was unprotected, the pertinent Fmoc-amino acid was added to it and the coupling reagents. Depending on the difficulty the synthesised sequence presented, two different combination of reagents were used:

HOBt and DIPCDI, in the molar proportion 1:1, with the Fmoc-amino acid.

HOBt, DIEA and 2-(1H-benzotriazol-1-il)-1,1,3,3-tetramethyluronium tetrafluoroborate (TBTU), in the molar proportion 1:2:1.

All the reagents were used in an excess of 2.5 times with respect to the quantity necessary.

In both cases the reaction was left for 1 hour, the conclusion being controlled by means of the ninhydrin test for the disappearance of the free amino groups (yellow colouring). When the reaction was not complete, the mixture was left in contact with the resin for 1 more hour, after which the ninhydrin test was repeated. In the event that there were still free amino groups in the resin, the latter was washed several times with DMF and the reagents were added again in half the quantity initially employed. On some occasions, and despite the reaction being repeated, incomplete couplings were produced. In order to be able to continue with the synthesis without anomalous chains being formed, it was necessary to block the incomplete chains by acetylation of the amino groups that still remained free. To this end, the resin was treated with 2 mequivalents of acetic anhydride and 1 mequivalent of 4-DMAP for each mequivalent of peptidyl-resin during 30 minutes. Next it was washed with DMF and a ninhydrin test was run to check the total disappearance of the amino groups (yellow colouring).

The ninhydrin test was substituted by the chloranil test in the event of detecting secondary amino groups of amino acids like proline, since the ninhydrin does not react with said groups.

EXAMPLE

Sysnthsis of the Peptides with Terminal Amino End

The peptides with carboxamide end are obtained from the resin p-methylbenzhydrylamine (MBHA). This resin needs a special initial treatment which comprises various washings with an acidic mixture of DCM/TFA at 40%, being left finally in contact with the resin for 20 minutes. Afterwards, to remove the acid, it was washed 5 times with DCM for 1 minute each time, and to neutralise it, the resin was treated with the base mixture DCM/diisopropylethylamine (DIEA) at 5%, until it was found that the resin pH was base. Finally, to remove the DIEA, it was washed various times with DCM.

Next, the coupling was carried out of the acidic spacer p-[(R,S)-alpha[1-9H-fluorene-9-e)-methoxy formamide]-2, 4-dimethoxybenzyl]-phenoxyacetic (AM), protected with the Fmoc group, which is what provides the sequence with its amide end. For this, the Fmoc-AM was weighed in an excess of 1.5 times the quantity required, and it was added to the resin together with the reagents hydroxybenzotriazole (HOBt) and DIPCDI (1:1, molar), also in excess, leaving the reaction to take place for 90 minutes. The conclusion of the reaction was determined by means of the Kaiser test or ninhydrin test, checking for the disappearance of free amino groups from the resin. In the event that all the spacer had not linked, the reaction was repeated once more, using half of the initial quanity of reagents employed. Once all the spacer had linked, the resin was washed various times with DMF in order to remove the reagents in excess.

The coupling of the remaining Fmoc-amino acids was performed through successive stages of deprotection of the amino group and of amide link formation, just as described in Example 1.

EXAMPLE 3

Deprotection and De-anchoring of the Peptide

For the deprotection of the free peptide sequence, the Fmoc: group is first removed from the terminal-amino end following the protocol given in the table below:

TABLE 2

Deprotection and de-anchoring protocol of the peptide

| Step | Reagent | Repetitions | Time |
|---|---|---|---|
| 1 | DMF | 3 times | 1 minute |
| 2 | DMF/piperidine 20% | 1 time | 1 minute |
| 3 | DMF/piperidine 20% | 3 times | 5 minutes |
| 4 | DMF | 3 times | 1 minute |
| 5 | DCM | 3 times | 1 minute |
| 6 | Tertiary amyl alcohol | 3 times | 1 minute |
| 7 | Ether | Until dry | |

In some syntheses the DMF/piperidine at 20% is replaced with the mixture DMF/piperidine/DBU (48:2:2, v/v/v), which is left in contact with the peptidyl-resin for 7 minutes.

Next the peptide was de-anchored from the resin and the protector groups removed from the amino acid functional chains, in a single step. To achieve this, various TFA mixtures were prepared with different scavengers like anisol, thioanisole, phenol, mercaptoethanol, and water, according to the protector groups present in the peptide chains. An aliquot was weighed of the peptide-resin a syringe with filter coupled to a vacuum system and the acidic mixture of scavengers added to it, being left in contact with the resin for 2 to 3 hours, at room temperature with occasional stirring. After this time elapsed, resin was filtered and washed 3 times with TFA, the filtrates and the washing products being collected in a tube. First the TFA was evaporated off with Nitrogen and afterwards cold diethyl ether was added, obtaining a white precipitate (free peptide). The precipitate was centrifuged at 3000 rpm for 15 minutes, the supernatant being drained off and the process repeated 5 more times. Finally the traces of ether were removed from the solid with Nitrogen, it was re-dissolved in water or acetic at 10%, depending on the peptide solubility, and lyophilised to obtain the raw free peptide product completely dry.

EXAMPLE 4

Hydrophobic Derivatization of the Peptide Sequences in Solid Phase

The fatty acids were coupled to the sequences in the same form as the Fmoc-amino acids, by means of the formation of an amide bond with the carboxylic group of the fatty acid.

Thus, an aliquot was weighed of the peptidyl-resin in a syringe with filter attached to a vacuum pump and was swollen with DMF. Next the deprotection of the Fmoc group was carried out. Once deprotected, the fatty acid employed in each case was added, in an excess of 2.5 times, together with the systhesis reagents DPCDI/HOBt or, TBTU/DIEA/ HOBt, depending on the peptide sequence in question. The conclusion of the reaction was determined, just as during the synthesis, by the ninhydrin test for disappearance of free amine groups.

To obtain the free hydrophobic derivative, the peptidyl-resin was treated with the same acidic mixture of TFA and scavengers, and under identical conditions to those employed in the de-anchoring of the initial peptide sequence.

EXAMPLE 5

Obtaining Liposomes Containing Doxorubicin and a Lipopeptide covering the Surface of the Liposome Initially, and in all cases, large multilamellar liposomes (MLV) were prepared following the method described by Bangham. From these, and by sonication, the small unilamellar liposomes (SUV) were obtained.

All the material and the solutions employed were sterile and, during the whole process, the work was carried out under a laminar flow hood to maintain sterility.

The liposomes prepared with the hydrophobic derivatives of the two active sequences had in their composition: phosphatidyl choline (PC), phosphatidyl glycerol (PG), cholesterol and Chroman-6. To obtain them the following procedure was adopted:

Thus, in the first place, SUV liposomes were prepared. The PC, PG, cholesterol and the Chroman-6 were weighed, and dissolved in Chloroform, the solvent being evaporated off in the rotary evaporator in order to form a lipid film. Any traces of solvent that might remain were removed by lyophilisation lasting 1 hour.

After this period had elapsed, the film was hydrated with 1 mL of NaCl at 0.9%, maintaining the ball in a bath at 60 degrees Celsius for 1 hour. To the MLV liposomes obtained, 1.2 mL of a Doxorubicin solution was added having a concentration equal to 2 mg/mL (2.4 mg). The preparation was left in repose for 15 minutes in a bath at 60 degrees Celsius and afterwards the ball was kept in a vacuum-free rotary evaporator which turned slowly for a period of 20 minutes.

In order to obtain SUV liposomes, the MLV were subjected to sonication in an ultrasonic bath for 8 cycles each lasting 2 minutes, separated by 5-minute intervals of repose in a bath at 60 degrees Celsius.

The incorporation of the lipopeptides was carried out by mixing an aliquot of 200 μL of liposomes, 200 μL of NaCl at 0.9% and 12 μL of a solution of lipopeptide in DMSO (c=10 mg/mL). The mixture was left in repose at 60 degrees Celsius for one hour and afterwards at room temperature for a further 30 minutes.

Alternatively, the liposomes were prepared incorporating the lipopeptide from the beginning. Thus, the PC, PG, Cholesterol and Chroman-6 lipids were mixed with an aliquot of the lipopeptide dissolved in chloroform/methanol, in the same molar ratio as in the previous case. The rest of the procedure is identical to the previous case.

Finally, to remove the Doxorubicin not encalsulated and the lipopeptide not incorporated, the sample was placed in a PD-10 column (Sephadex G-25). For this, the column was first balanced with NaCl at 0.9%. Once balanced, the sample was added, which was also eluted with NaCl at 0.9%, until it overflowed from the column. The volume of liposomes obtained was made up to 2 mL.

Following this process, the following types of liposomes were prepared incorporating Doxorubicin:

EXAMPLE 6

Obtaining Liposomes Containing Paclitaxel and a Lipopeptide Coating the Surface of the Liposome Initially, and in all cases, large multilamellar liposomes (MLV) were prepared following the method described by Bangham. From these, and by sonication, small unilamellar liposomes were obtained.

All the material and the solutions employed were sterile and, during the whole process, the work was carried out under a laminar flow hood to maintain sterility.

The liposomes prepared with the hydrophobic derivatives of the active sequences had in their composition: phosphatidyl choline (PC), phosphatidyl glycerol (PG) and cholesterol. To obtain them the following procedure was adopted:

Thus, in the first place, SUV liposomes were prepared. The PC, and cholesterol were weighed, and dissolved in Chloroform, the solvent being evaporated off in the rotary evaporator in order to form a lipid film. Any traces of solvent that might remain were removed by lyophilisation lasting 1 hour.

After this period had elapsed, the film was hydrated with 1 mL of NaCl at 0.9%, maintaining the ball in a bath at 60 degrees Celsius for 1 hour. To the MLV liposomes obtained, 1.2 mL of a Paclitaxel solution was added having a concentration equal to 0.5 mg/mL (0.6 mg). The preparation was left in repose for 15 minutes in a bath at 60 degrees Celsius and afterwards the ball was kept in a vacuum-free rotary evaporator which turned slowly for a period of 20 minutes.

In order to obtain SUV liposomes, the MLV were subjected to sonication in an ultrasonic bath for 8 cycles each lasting 2 minutes, separated by 5-minute intervals of repose in a bath at 60 degrees Celsius.

The incorporation of the lipopeptides was carried out by mixing an aliquot of 200 μL of liposomes, 200 μL of NaCl at 0.9% and 12 μL of a solution of lipopeptide in DMSO (c=10 mg/mL). The mixture was left in repose at 60 degrees Celsius for one hour and afterwards at room temperature for a further 30 minutes.

Alternatively, the liposomes were prepared incorporating the lipopeptide from the beginning. Thus, the PC, PG and Cholesterol lipids were mixed with an aliquot of the lipopeptide dissolved in chloroform/methanol, in the same molar ratio as in the previous case. The rest of the procedure is identical to the previous case.

Finally, to remove the Paclitaxel not encapsulated and the lipopeptide not incorporated, the sample was placed in a PD-10 column (Sephadex G-25). For this, the column was first balanced with NaCl at 0.9%. Once balanced, the sample was added, which was also eluted with NaCl at 0.9%, until it overflowed from the column. The volume of liposomes obtained was made up to 2 mL.

| Lipid composition | Conc. of Lipids | Conc. of drug | Coating lipopeptide | Conc. of peptide | Liposome size |
|---|---|---|---|---|---|
| PC/PG/Chol./Chr. | 9.91 mg/mL | 1.04 mg/mL | Myristic-(A)$_5$-CYESIKVAVS (SEQ ID NO: 8) | 0.42 mg/mL | 160 nm |
| PC/PG/Chol./Chr. | 14.05 mg/mL | 1.5 mg/mL | Myristic-PEAGD (SEQ ID NO: 6) | 1.1 mg/mL | 115 nm |

Following this process, the following types of liposomes were prepared incorporating Paclitaxel:

| Lipid composition | Conc. of Lipids | Conc. of drug | Coating lipopeptide | Conc. of peptide | Liposome size |
|---|---|---|---|---|---|
| PC/PG/Chol. | 8.93 mg/mL | 0.26 mg/mL | Myristic-(A)$_5$-CYESIKVAVS (SEQ ID NO: 8) | 0.42 mg/mL | 140 nm |
| PC/PG/Chol. | 13.5 mg/mL | 0.4 mg/mL | Myristic-PEAGD (SEQ ID NO: 6) | 1.1 mg/mL | 105 nm |

EXAMPLE 7

Cellular Adhesion Tests

Solutions of Laminin-1 and synthetic peptides (50 mg/well) were fixed in wells of the 96-well tissue culture plate of TPP (Switzerland). The wells were dried at room temperature during the night. Before using them, the wells were washed with tamponed saline solution free from Calcium and Magnesium ions. The remaining free radicals of the polystyrene were blocked by using a 1% BSA solution.

They were cultivated and marked with $^{51}$Cr cells of human fibrosarcoma HT1080. The marked cells were placed (1 cpm/well) in the wells which contained the Laminin and the synthetic peptides.

After 30 minutes of incubation at 37 degrees Celsius, the unadhered cells were removed by washing. The adhered cells were smoothed and the radioactivity measured. The specific percentages of adhesion encountered are shown in the attached FIG. 1.

EXAMPLE 8

Figure 2:
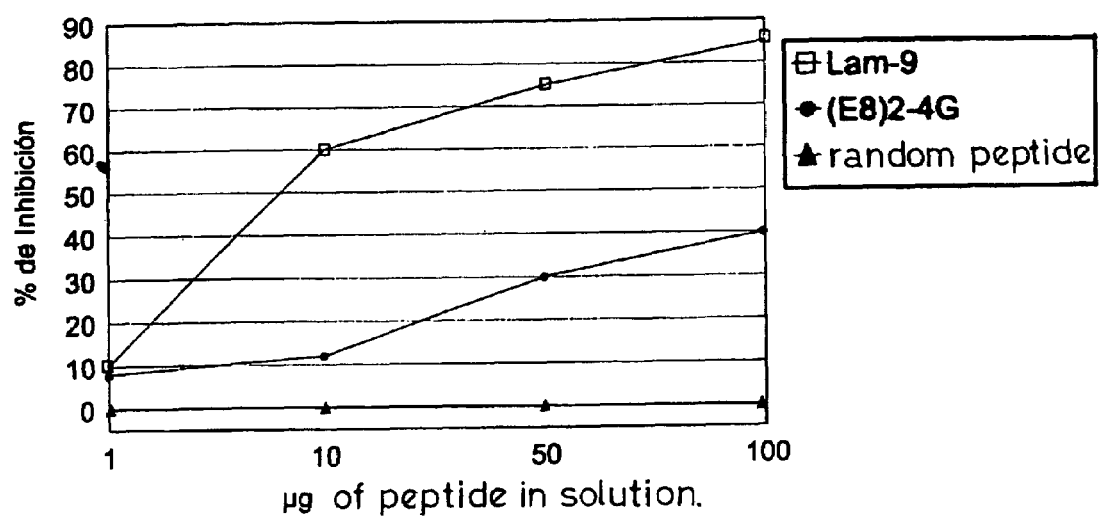

Inhibition of Cellular Adhesion to Laminin (Complete Molecule) in Vitro by Peptides of the Laminin Following the procedure described under Example 1 HT-1080 cells marked with $^{51}$Cr were adhered, in wells (0.32 cm$^2$) coated with 1 µg of Laminin. The adhered cells were incubated with different concentrations of of synthetic peptide fragments of Laminins. The results obtained are shown in the attached FIG. 2.

EXAMPLE 9

Anti-proliferative Effect of Doxorubicin Liposomes Directed Against Specific Receptors of Laminin Peptides in Tumoral Cells The anti-proliferative effect of Doxorubicin was analysed by following the MTT method. HT1080 cells obtained from exponential cultures were sown in 0.36 cm$^2$ wells (96-well tissue culture plates of TPP, Switzerland) with a density of 5000 cells per well. One day later, the cells were washed and incubated for two hours with liposomes containing Doxorubicin. The different liposome formulations were adapted to the same drug concentration and the test was carried out in parallel wells (increasing the concentration of Doxorubicin from 0.01 µg/ml to 10 µg/ml. After the incubation, the cells were washed five times with PBS and incubated for three days in a complete medium. After this period, to each well was added 50 µL of PBS containing 1 mg/ml of MTT (tetrazolium salt, Sigma) and they were incubated for a further four hours. The intracellular crystals of Fromazan resulting from the reduction of the tetrazolium salt, only present in the active cells, were dissolved in DMSO. The number of metabolically active cells was estimated by measuring the absorbance of this solution of DMSO at 540 nm.

The percentage of cytostatic activity was calculated according to the formula $(A-B)/A \times 100$, where A is the absorbance in tumoral cells incubated in a control medium and B is the absorbance in tumoral cells incubated with the liposome preparations.

Figure 3:
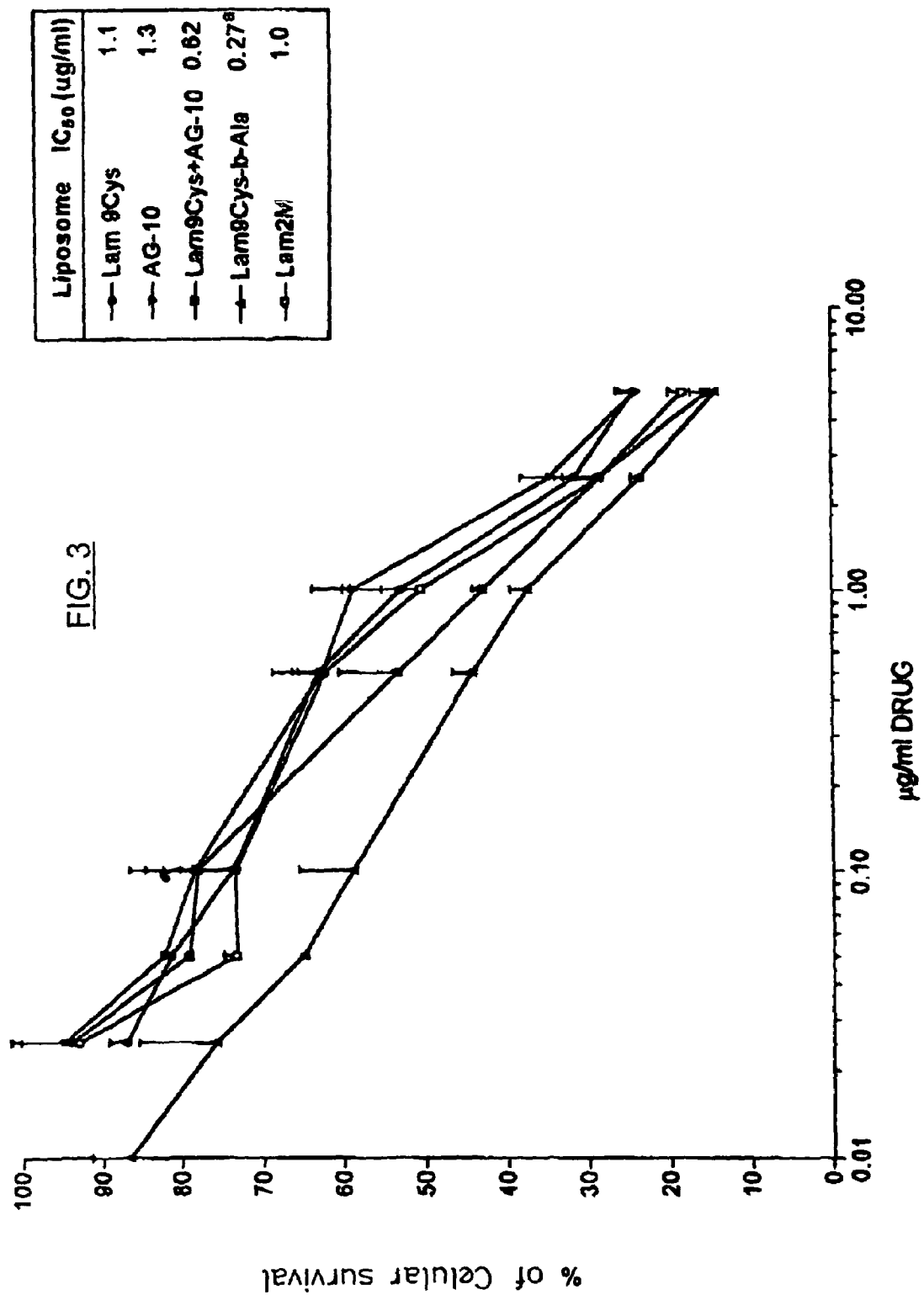

The results of the resulting cytostasis are shown in the attached FIG. 3, in which:
the results present the mean+/−the standard desiccation of three independent experiments performed in triplicate;
The IC$_{50}$ is defined as the drug concentration at which 50% of the cells survive in comparison with the control lot; and
$P>0.05$; Student test t.

EXAMPLE 10

Biodistribution of Doxorubicin Administered as Free Drug or Liposome Preparation (PC/PG/Chol/myristoyl-AAAAACYESIKVAVS)/Doxorubicin) in Tumour-bearing Animals Animals: The tests were performed on naked and immunosuppressed BALB/c mice obtained for the animal production area of IFFA CREDO Inc. (Lyons, France). The animals were kept in laminar flow cabins in pathogen-free conditions and were used when they reached an age of 8 weeks.

Cellular culture conditions: Cells of HT1080 human fibrosarcoma were made to grow in Ham's F-12 medium (GIBCO, Grand Island, N.Y.) supplemented with 10% of bovine fetal serum, Sodium pyruvate, non-essential amino acids, L-glutamine, and vitamin solution (GIBCO, Grand Island, N.Y.). The cultures were kept in plastic and incubated in 5% CO2–95% air at 37 degrees Celsius in humidified incubators. The cellular line was examined to certify the absence of Mycoplasma.

The tumoral cells were harvested from the sub-confluent cultures (50–70% confluence) by treating with trypsin (0.25%) and EDITA (0.02%). The cells were washed in a supplemented medium and afterwards were re-suspended in a Hank Balanced Saline Solution (HBSS) for their subsequent injection. Only monocellular suspensions with a viability of more than 90% (determined by colouring with Trypan blue) were used for the in vivo studies.

Figure 4:
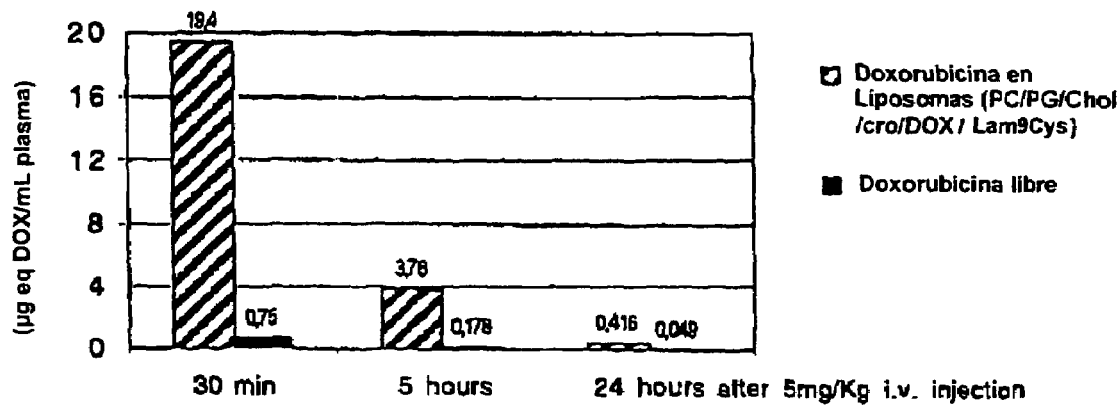
Figure 5:
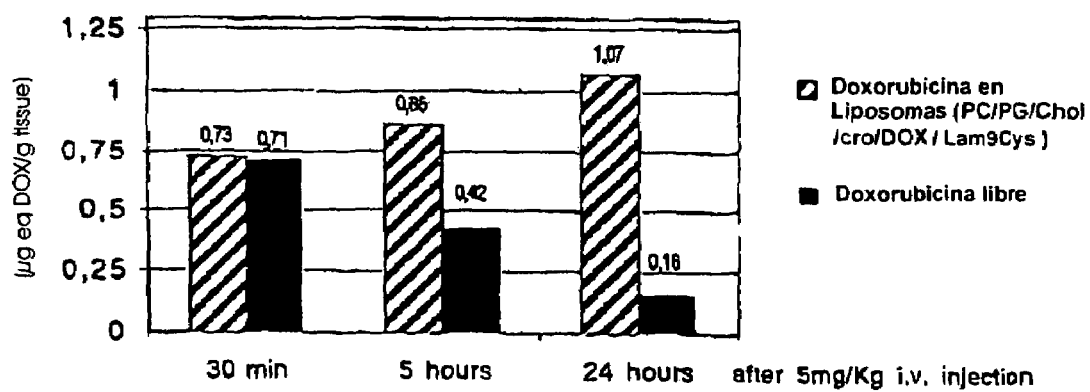

Biodistribution test: HT-1080 cells at a concentration of 1×107 cells/mL of HBSS were pre-mixed with an equal volume of liquid Matrigel (Collaborative Biomedical Products, Bedford, Mass.) 10 mg/mL. Of the resulting suspension, 0.02 mL were inoculated subcutaneously into the left-hand flank of the mice. Tumour growth was monitored twice weekly. When the tumours attained a volume of 1 cm$^3$ (day 25 after injection of the cells), the mice received a single intravenous dose of Doxorubicin (5 mg/kg) in liposome preparation or free drug form. At times of 30 minutes, 5 hours and 24 hours from the administration of the drug, the mice were sacrificed and samples were taken of tumoral tissue and plasma. The results obtained are shown in FIGS. 4 and 5 attached.

The invention claimed is:

1. A liposome encapsulating at least one anticancerous drug and coated with a lipopeptide composed of three substructures: a lipid fragment, a biologically active oligopeptide and an oligopeptide spacer between and bound to the lipid fragment and the active oligopeptide wherein the active oligopeptide is SEQ ID NO: 4 and the oligopeptide spacer is selected from the group consisting of SEQ ID NO: 1, SEQ ID NO: 2, and SEQ ID NO: 3.

2. The liposome of claim 1, wherein the lipid fragment of the lipopeptide comprises fatty acids of carbon chain length between C6 and C20.

3. The liposome of claim 1, wherein the lipid fragment of the lipopeptide comprises a lipid selected from the group consisting of: decanoyl, myristoyl and stearoyl.

4. The liposome of claim 1, wherein the oligopeptide spacer is SEQ ID NO: 1 bound to active oligopeptide SEQ ID NO: 4 to form SEQ ID NO: 5.

5. The liposome of claim 1, wherein the ratio of total lipids forming the liposome to the anticancerous drug is between 20:1 and 2:1.

6. The liposome of claim 1, wherein the ratio of total lipids forming the liposome to the anticancerous drug is 10:1.

7. The liposome of claim 1, wherein the lipid fragment comprises phospholipids, of both natural and synthetic origin, and cholesterol.

8. The liposome of claim 7, wherein the phospholipids present are a combination of neutral and negatively charged phospholipids.

9. The liposome of claim 8, wherein the neutral phospholipid is phosphatidylcholine.

10. The liposome of claim 8, wherein the negatively charged phospholipid is phosphatidylglycerol.

11. The liposome of claim 8, wherein the ratio of the neutral phospholipids to the negatively charged phospholipid is between 10:2 and 10:10.

12. The liposome of claim 8, wherein the ratio of the neutral phospholipids to the negatively charged phospholipid is between 10:7 and 10:10.

13. The liposome of claim 7, wherein the proportion of cholesterol, with respect to the total amount of lipids, is between 0 and 50%.

14. The liposome of claim 7, wherein the proportion of cholesterol, with respect to the total amount of lipids, is between 35 and 50%.

15. The liposome of claim 1 further containing at least one inhibitor of lipid peroxidation.

16. The liposome of claim 15, wherein the inhibitors of lipid peroxidation are Vitamins and their derivatives.

17. The liposome of claim 16, wherein the inhibitors of lipid peroxidation are selected from the group consisting of Vitamin E, Vitamin E acetate, BHT, chroman and chromen.

18. The liposome of claim 17, wherein the chromen is 3,4-dihydride-2,2-dimethyl-6-hydroxy-7-methoxy-2H-1-benzopyrane.

19. The liposome of claim 17, wherein the proportion of lipopeptide with respect to the total amount of lipids is between 0.1% and 30%.

20. The liposome of claim 19, wherein the proportion of lipopeptide with respect to the total amount of lipids is between 1% and 15%.

21. The liposome of claim 1, having an average size between 50 nm and 250 nm.

22. The liposome of claim 1, wherein the anticancerous drugs are selected from the group consisting of: nirogenated mustard analogues, cyclophosphamide, melphalan; phosphamide, trophosphamide, ethylenimines, thiotepa, nitrosoureas, carmustine, temozolomide, dacarbazine, antimetabolite analogues of folic acid, methotrexate, raltitrexed, purine analogues, thioguanine, cladribine, fludarabine, pyrimidine analogues, fluorouracil, florafur, gemcitabine, alkaloids of vinca or analogues thereof, vinblastine, vincristine, vinorelbine, podophyllotoxin derivatives, etoposide, taxanes, docetaxel, paclitaxel, anthracyclines, doxorubicin, epirubicin, idarubicin, mitoxantrone, cytotoxic antibiotics, bleomycin, mitomycin, platinum compounds, cisplatin, carboplatin and oxaliplatin, monoclonal antibodies, rituximab, pentostatin, miltefosine, estramustine, topotecan, irinotecan and bicalutamide.

23. A method of treating a malignant tumor in a mammal comprising administering intravenously to said mammal a pharmaceutically effective amount of the liposome of claim 1.

24. The method of claim 23, wherein said mammal is a human.

* * * * *